(12) United States Patent
Vert et al.

(10) Patent No.: US 8,709,481 B2
(45) Date of Patent: Apr. 29, 2014

(54) SYSTEM FOR CONTROLLED RELEASE OF AN ACTIVE PRINCIPLE AND METHOD FOR PREPARATION

(75) Inventors: Michel Vert, Castelnau-le-lez (FR); Laurent Leclercq, Montpellier (FR); Mahfoud Boustta, Pignan (FR)

(73) Assignees: Centre National de la Recherche Scientifique, Paris (FR); Univeriste de Montpellier 1, Monpellier (FR)

( * ) Notice: Subject to any disclaimer, the term of this patent is extended or adjusted under 35 U.S.C. 154(b) by 379 days.

(21) Appl. No.: 12/669,252

(22) PCT Filed: Jul. 18, 2008

(86) PCT No.: PCT/FR2008/001066
§ 371 (c)(1),
(2), (4) Date: Apr. 1, 2010

(87) PCT Pub. No.: WO2009/037401
PCT Pub. Date: Mar. 26, 2009

(65) Prior Publication Data
US 2010/0260848 A1  Oct. 14, 2010

(30) Foreign Application Priority Data
Jul. 18, 2007 (FR) ..................... 07 05187

(51) Int. Cl.
*A61K 9/14* (2006.01)
*A61K 47/48* (2006.01)
*A61K 9/20* (2006.01)

(52) U.S. Cl.
CPC ......... *A61K 47/482* (2013.01); *A61K 47/48207* (2013.01); *A61K 9/204* (2013.01); *A61K 9/2045* (2013.01)
USPC ........................................... 424/486

(58) Field of Classification Search
None
See application file for complete search history.

(56) References Cited

U.S. PATENT DOCUMENTS

| 4,265,247 | A | 5/1981 | Lenz et al. | |
|---|---|---|---|---|
| 5,026,821 | A | 6/1991 | Boustta et al. | |
| 6,884,438 | B1 * | 4/2005 | Quintanar et al. | 424/490 |
| 7,018,649 | B2 * | 3/2006 | Tavares et al. | 424/449 |
| 7,125,837 | B1 * | 10/2006 | Keating et al. | 514/13.5 |
| 2005/0118718 | A1 | 6/2005 | Bae et al. | |
| 2005/0266077 | A1 * | 12/2005 | Royer | 424/469 |

FOREIGN PATENT DOCUMENTS

| EP | 332530 A1 | 9/1989 | |
|---|---|---|---|
| WO | 92/11844 A | 7/1992 | |
| WO | WO 92/11844 * | 7/1992 | ............... A61K 9/26 |
| WO | 2006/099514 A2 | 9/2006 | |

OTHER PUBLICATIONS

Gac-Breton et al., J. Drug Targeting, 2004, 12(5), pp. 297-307.*
Cabrera et al., Biochem. Engin. J., 2005, vol. 25, pp. 165-172.*
T. Etrych, M. Boustta, L. Leclercq and M. Vert, Release of Polyanions from Polyelectrolyte Complexes by Selective Degradation of the Polycation, Journal of Bioactive and Compatible Polymers, Mar. 2006, pp. 89-105, vol. 21, Sage Publications.
L. Leclercq, M. Boustta and M. Vert, Degradable polymers as Tools for Polyelectrolyte Complex Analysis, American Chemical Society, 2006, pp. 267-279.
X. Loan and R. Bodmeier, Influence of the poly(lactide-co-glycolide) type on the leuprolide release from in situ forming microparticle systems, Journal of Controlled Release, 2006, pp. 266-272, Elsevier Science B.V.
H. Rossignol, M. Boustta and M. Vert, Synthetic poly(p-hydroxyalkanoates) with carboxylic acid or primary amine pendent groups and their complexes, International Journal of Biological Macromolecules, 1999, pp. 255-262, Elsevier Science B.V.
S. Gimenez, S. Ponsart, J. Coudane and M. Vert, Synthesis, Properties and in vitro Degradation of Carboxyl-Bearing PCL, Journal of Bioactive and Compatible Polymers, Jan. 2001, pp. 32-46, vol. 16, Technomic Publishing Co., Inc.
J. Mauduit, M. Boustta and M. Vert, Hydrolytic degradation of benzylated poly(B-malic acid): Influence of sample size, sample shape, and polymer composition, 1995, pp. 207-220, VSP.
L. Brannon-Peppas and M.Vert, Polylactic and Polyglycolic Acids as Drug Delivery Carriers, Handbook of Pharmaceutical Controlled Release Technology, 2000, pp. 100-130, Marcel Dekker, Inc., New York, NY.
M. Vert, Biopolymers and Artificial Biopolymers in Biomedical Applications, an Overview, Biorelated Polymers: Sustainable Polymer Science and Technology, 2001, pp. 63-79, Kluwer Academic/Plenum Publishers.
International Search Report in Corresponding Application PCT/FR2008/001066 Dated Feb. 12, 2009.
French Search Report in Corresponding Applications FA 695347 and FR 070518 Dated Mar. 10, 2008.

* cited by examiner

*Primary Examiner* — Brian Gulledge
(74) *Attorney, Agent, or Firm* — Young & Thompson

(57) ABSTRACT

A system for controlled release of an active principle, includes at least (a) a degradable polymer matrix which produces acid compounds and (b) at least one acid-sensitive complex of an active principle having at least one electrostatic charge and a complexing polyelectrolyte partner of opposite charge which complexes with the active principle. A method for preparation of such a system is described. The release of the active principle (7P) is prolonged over 18 days (ternary system PMLA/7P/PLAGA) in comparison to binary systems (7P/PLAGA) and (PMLA/7P).

15 Claims, 3 Drawing Sheets

Figure 2
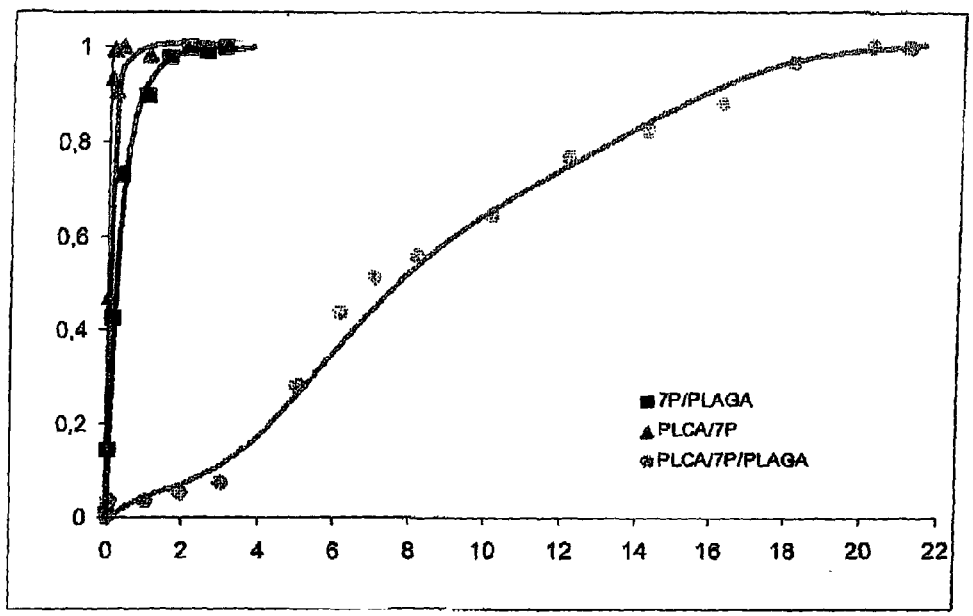
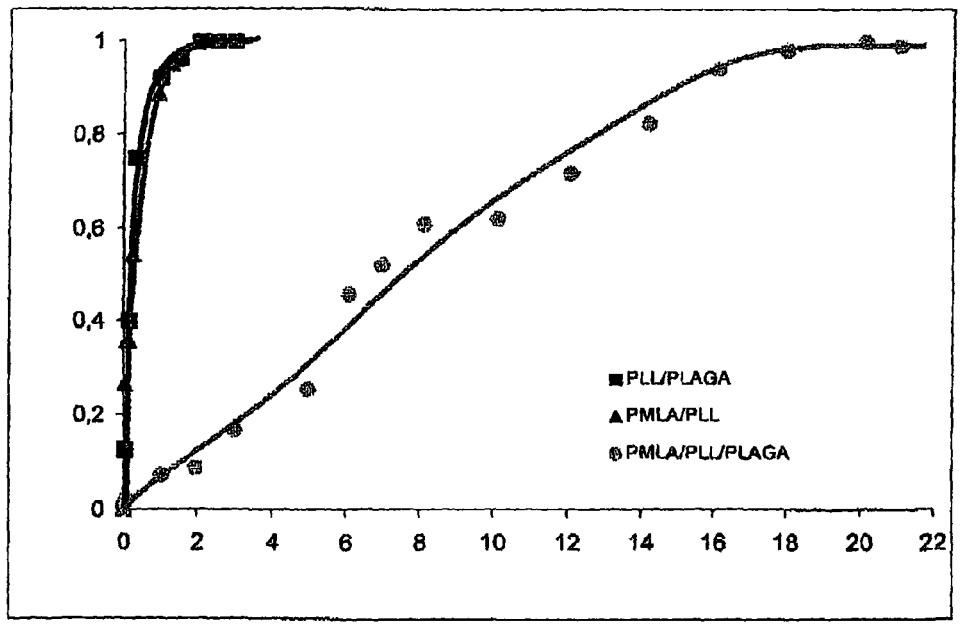
Figure 3

SYSTEM FOR CONTROLLED RELEASE OF AN ACTIVE PRINCIPLE AND METHOD FOR PREPARATION

FIELD OF THE INVENTION

The present invention relates to a system for the controlled release of an active principle comprising a degradable polymer matrix and a solid complex of said active principle and an acid-sensitive polyelectrolyte partner, said partner being in turn degradable under the effect of the degradation products of the polymer(s) forming the matrix.

In the field of the controlled release of active principles, particularly active principles comprising multiple electrostatic charges, or polyelectrolytes, such as peptides, proteins and polynucleotides, it has been proposed to trap the active principle temporarily in a matrix, generally a polymer, from which the active principle molecules are released according to a profile determined by the solubility thereof as a function of phase partition, of the ability thereof to diffuse within said matrix or defects contained therein, and/or of the degradation rate thereof [3].

However, the incorporation of highly hydrosoluble macromolecular compounds, such as peptides and protein and oligo- or polynucleotide type macromolecules, is frequently difficult and ineffective due to the hydrophilicity thereof. In parallel and for the same reasons, the release is frequently too rapid due to the high solubility thereof in surrounding biological fluids or very significant swelling of the matrix, such as in the case of hydrogel type polymer matrixes.

Furthermore, trapping highly hydrophilic active principles, particularly electrostatically charged active principles (anions or cations) is difficult to carry out as these active principles are difficult to incorporate in a solid hydrophobic matrix and the release thereof is too rapid or too long depending on the nature of the active principle-matrix system.

Finally, the release profiles have been generally unsatisfactory to date and there is a need for controlled release systems with a more suitable release profile. The Applicant has met this need and achieved this aim for active principles carrying at least one electrostatic charge, using polymer matrixes which are degradable by means of hydrolytic degradation with acid compound formation. Unlike the general scenario whereby the active principle is incorporated directly in the matrix, according to the invention, the active principle is first inserted, with a polyelectrolyte partner of opposite charge, into a solid polyelectrolyte complex. The matrix is degraded in contact with water or physiological fluids, forming acids which catalyse the degradation of the complexing polyelectrolyte, and the active principle is released.

BACKGROUND OF THE INVENTION

WO 2006/099514 describes controlled release systems wherein an active principle and a bioactive polyelectrolyte complex (PEC) are added independently from each other to a polymer solution. They are incorporated in the polymer matrix in solution, by means of dissolution or dispersion. This document does not describe or suggest the specific use of acid-sensitive complexing agent, which interacts with the acid degradation products of the matrix. In WO 2006/099514, PECs, incorporated in polymer matrixes, modulate the release of a separate active principle from the PECs. These PECs are stable solids and can thus be considered to be bioactive. Furthermore, they cannot diffuse as such out of a polymer matrix of any kind. For this to be possible, the PEC must be destabilised and this is known to be very difficult.

According to the invention, one of the partners of the complex is chosen to be degradable to this end.

Complexing may particularly mask excessive hydrophilicity and promote the incorporation of the active principle in the matrix. The incorporation of the complex in a matrix makes it possible to protect the complexed active principle temporarily, impede or prolong the delivery thereof and prevent a sudden initial release.

SUMMARY OF THE INVENTION

According to the invention, a complexing polyelectrolyte type polymer partner, that is degradable by a hydrolytic process, temporarily fixes an active principle, in solid form, within a polymer matrix. In contact with water or a physiological medium, the active principle is released progressively, by means of the degradation of the acid-sensitive polyelectrolyte complexing agent under the effect of the acid degradation products of the matrix.

The conditions are thus fulfilled to protect the ionic physiologically active principle or the polyelectrolytic bioactive substance by complexing with an acid-sensitive polyelectrolyte of opposite net charge. This protection is provided without making use of chemical coupling which would create a new entity, whereas such an entity would need to be approved by the regulatory bodies.

The active principle or bioactive compound thus placed in the form of solid complex particles is rendered insoluble in aqueous medium, which minimises the sudden initial release. In this way, preferably, the complex is particulate, solid and stable under the pH, temperature and salinity conditions of physiological media. According to the invention, the complexes are preferably precipitated or obtained in the solid state by means of freeze-drying or oven drying, for example.

Furthermore, according to the invention, the complex is temporarily trapped by incorporating same in a matrix. This second protection of the active principle enables a delayed release essentially determined by the degradation rate of the polyelectrolyte and that of the hydrolytically degradable matrix, without any chemical modification of the bioactive compound.

According to the invention, the phenomena involved are of the cooperative type in that complexing is performed in a very limited range of physicochemical characteristics (pH, pK(s) of the ionizable or ionized functions, temperature, ionic force, type of counter-ions and co-ions, which are present, ionic component charge density, and frequently order of reagent addition). Consequently, a polyelectrolytic complex is generally stoechiometric in terms of opposite electric charges and not in terms of weight.

On the contrary, the mixture in terms of weight, as used in the prior art almost inevitably results in excesses of one of the components of opposite signs, the excess in this case being subject to the same rules as the non-complexed compound and released according to the diffusion (or matrix degradation) rules.

Furthermore, the destabilisation of a complex does not obey the concept of mass, but a relatively sudden variation of the external conditions (variation of pH and/or ionic force).

In this way, it is observed on the basis of curves disclosed in the document WO 92/11844 that there is no prolonged release after 24 hours, which is conveyed by a horizontal variation of the EPO concentration over time. The only release observed is of the "burst" type and the release stops at 30% or 70% depending on the composition. Also, apart from "burst" type release differences, the BSA-sucrose (neutral) and BSA-protamine (polybase) release profiles are similar and it can be concluded that the mixtures are produced by weight and not by charges and that the electrostatic charges controlling the complexing are not taken into account.

Furthermore, in the document WO 92/11844, the complexes described are not precipitated but are in solution, the solutions being percolated through chromatography columns.

In this way, the invention proposes a system for the controlled release of an active principle comprising at least (a) one degradable polymer matrix forming acid compounds and (b) at least one complex of an active principle having at least one electrostatic charge and a polyelectrolytic partner of opposite charge which complexes with the active principle, of opposite charge, the complexing agent being acid-sensitive.

The present invention also relates to the use of an acid-sensitive polyelectrolyte as a complexing agent, in a system for the controlled release of an active principle comprising at least one degradable polymer matrix forming acid compounds and at least one complex between an active principle having at least one electrostatic charge and a polyelectrolyte partner which complexes with said active principle, of opposite charge.

Moreover, the invention proposes a method for the preparation of a controlled release system comprising at least the steps consisting of the formation of a complex between an active principle having at least one electrostatic charge and a complexing polyelectrolyte partner of opposite charge, the complex being preferably in solid form and said complexing agent being acid-sensitive, followed by the incorporation of the complex in a bioabsorbable polymer matrix forming acid degradation products.

It is thus possible to form, by means of ionic pairing, a degradable complex, stable under the pH, salinity and temperature conditions of neutral physiological media, for example in the form of a precipitate, which can be isolated and incorporated in a matrix. Such an ionic pairing requires a charge stoechiometry, as opposed to a mass stoechiometry.

The controlled release systems according to the invention make it possible to modulate the release features of the active principle, without any chemical modification of the bioactive compound, i.e. the active principle. The modulation is dependent on the stability of the polyelectrolyte partner of opposite charge to that of the active principle, the sensitivity of the complex to degradation in contact with acids and the type of matrix, the delayed release of the active ingredient being essentially determined by the degradation rate of the degradable polyelectrolyte and by the type of polymer matrix.

DETAILED DESCRIPTION OF THE INVENTION

These controlled release systems may particularly enable the controlled release of charged oligomer or polymer type active principles.

The formation of the complex is a decisive component of the preparation of the release systems according to the invention. The complex is preferably sufficiently stable under the conditions applied to make it possible to isolate and incorporate same in a matrix. More specifically, the complex is preferably, according to the invention, stable under typical pH, salinity and temperature conditions of the biological fluid in contact with the release system. This is particularly applicable, at pH 7.4 and approximately 37°, to blood or lymph. In this way, the term physiological media wherein the complex is stable refers to physiological media wherein the controlled release system is intended to be applied.

Preferably, a solid complex obtained in powder form is formed, for example by means of precipitation according to the invention. According to the invention, the complex is thus insoluble in aqueous preparation medium. The complex is incorporated in a degradable polymer matrix forming acid compounds, in a routine manner for those skilled in the art. The grain size must be compatible with the subsequent incorporation, for example by coating in the matrix material.

The solid complex may, in some cases, if it is not obtained by precipitation, be obtained for example in freeze-dried product form. The solid form of the complex is dependent on the complexing agent-active principle pair, and those skilled in the art will know how to select and adapt complex formation techniques with a view to the incorporation thereof in the matrix.

As a degradable polymer matrix, any biodegradable polymer suitable for forming acid compounds following the hydrolytic degradation thereof may be used.

As a general rule, poly(a-hydroxy acid) or polyanhydride type matrixes are suitable, and other similar polymers, that are physiologically acceptable and suitable for forming acid compounds following the degradation thereof may also be envisaged, such as some polyorthoesters. Such polymers are for example described by M. Vert as artificial biopolymers [8].

For example, poly(lactic acid-co-glycolic acid) (PLAGA) matrixes may be cited. This copolymer supplies lactic acid and glycolic acid during degradation. The term "PLA" refers to poly(lactic acid) and the term PLA50 commonly refers to 50% L-lactic units and 50% D-lactic units, PLA(37.5)GA (25) to 37.5% L-lactic units and 37.5% D-lactic units for the lactic acid units and 25% glycolic acid units. The greater the lactic acid content is, the more marked the hydrophobic nature of the matrix is and the slower the hydrolytic degradation is. For example, degradation in PBS medium typically ranges from 18 days with PLA(37.5)GA(25) to 90 days with the homopolymer PLA50 [7].

The initial molar mass of the matrix is selected to make it possible to form the desired implant or particles or hydrogel according to routine measures in the field of controlled release.

Poly(caprolactone) (PCL) matrixes may also be cited, particularly PCLs modified so as to be acid-sensitive, such as those described by Gimenez et al. [5]. PCL polymers supply caproic acid during degradation. As PCL is more hydrophobic than PLA, the degradation of this polymer is slower than that of PLA.

Suitably partially esterified copolymer derivatives of poly (β-malic acid) such as those cited by Mauduit et al. [6] may also be cited.

Hydrogels derived from the above polymers, particularly PLA and PLAGA, by combining with hydrophilic segments, may also be cited.

As mentioned above, any other matrix capable of supplying physiologically acceptable acid degradation products may be envisaged.

The degradable polymer matrix may be used in any standard form, such as implants, films, microparticles, hydrogels and particularly hydrophilic matrixes based on copolymers comprising hydrophilic segments such as poly(vinyl pyrrolidone), dextran or poly(ethylene oxide) and polymer segments forming acid compounds such as polyanhydrides or poly(α-hydroxy-acids), with the selected form enabling the incorporation of the acid-sensitive complex.

The term active principle or ionic bioactive compound capable of being released according to the present invention refers to any active principle or, more broadly, any ionic bioactive compound having at least one electrostatic charge, or any substance with polyelectrolytic properties, i.e. having at least one electrostatic charge.

The method according to the invention is particularly beneficial for enabling the controlled release of proteins, genes and DNA fragments, oligonucleotides, for example, including small peptides.

The ionic bioactive compound is associated with a polyelectrolyte partner which complexes with same, having an opposite charge. Preferably, the ionic bioactive compound is also a polyelectrolyte. Any ionic active principle or charged oligomer capable of forming a solid ionic or polyionic complex type combination may be used.

The polyelectrolyte partner must be acid-sensitive and have opposite charges so as to be able to form a polysalt type complex or polyelectrolytic type complex, which is solid and stable under the application conditions.

According to the invention, the term polyelectrolytic partner refers to any physiologically acceptable acid-sensitive polymer capable of complexing with the active principle.

According to the invention, a complexing agent is considered to be acid-sensitive if it is stable at a pH of 7.4 and is degraded at a pH below 7. A complexing agent that is degradable in an acid medium is thus considered to be acid-sensitive according to the invention.

The degradation is all the more rapid if the surrounding medium is acidic.

For example, the complexing agents PMLA, PLCA and PSA are degraded significantly when in contact with a pH below 6. For example, such a pH is found in intracellular lysosomal vacuoles.

Preferably, degradable and bioabsorbable, i.e. suitable for excretion by the pulmonary and/or renal route, polyelectrolytes are used. Thus, advantageously, the complexing acid-sensitive polyelectrolyte belongs to the family of polymers referred to as "artificial biopolymers" [8]. Such degradable, bioabsorbable and biocompatible polymers or copolymers consist of repetition units from monomers normally present in biochemical circuits and regenerated following hydrolytic degradation, said units being interlinked by intrinsically acid-sensitive chemical functions such as ester, particularly aliphatic ester, functions, anhydride functions, orthoester functions, or functions considered to be stable in aqueous media, such as amide or oside functions, when rendered acid-sensitive by the presence of other promoting functions in the formulas thereof.

The archetype of such polyester type artificial biopolymers is a polymer containing [—COO-]$_n$ within-chain bonds and a remainder of repetition units comprising at least one ionizable function such as carboxylic acid (example: PMLA) or basic function (example: PSA). The archetype of polymers rendered acid-sensitive by the presence of another function is PLCA, the COOH function rendering the polymer hydrosoluble and sensitising the within-chain [COHN—]$_n$ amide functions to acids and thus to acid media, whereas said functions are normally resistant whether in aliphatic or aromatic polyamide type polymers or in proteins, which require the involvement of enzymes.

For example, PMLA and PLCA type polymers may be used to complex any active principle or bioactive substance or oligomer having a positive net charge. PSA type polymers may be used to complex any active principle or bioactive substance or oligomer having a negative net charge. PMLA, PLCA, PLCAI and PSA polymers are acid-sensitive polyelectrolytes capable of complexing not only with oligomers or polymers having an opposite charge but also with acid or basic type compounds of interest such as peptides or DNA fragments. More specifically, PSA, PMLA and PLCA polymers are defined by the following units (1) to (4), PLCA units being obtained by means of hydrolysis of the units of the imide PLCAI (3), represented in table I below. The PLCA units (4) are combinations of lysine units and citric acid units. PMLA and PLCA are particularly known from U.S. Pat. No. 4,265,247 and EP 332 530 and PSA is described by Rossignol, H., et al. [4]. See also [1], [2] and [8].

Preferably, PMLA, PLCA, PLCAI and PSA polymers represented in table I below are used according to the invention. Other different Na$^+$ and Br$^-$ counter-ions may be used. Similarly, —COOH forms for polyacids and —NH$_2$ forms for polybases may be envisaged.

For complexing agents and for polymers matrixes, masses Mw of the order of 5000 to 500,000 g/mol may be envisaged, preferably of the order of the 10,000 to 100,000 g/mol.

Examples of ionic bioactive compounds according to the invention include peptides or proteins: bursin, leuprolide, triptorelin, other LH-RH analogues, protein fragments, protein kinase inhibitors, etc. The basic active principles also include multiamine type basic compounds other than peptides or proteins.

TABLE I

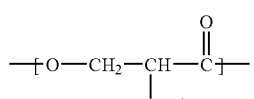 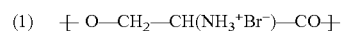

PSA

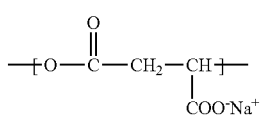 

PMLA

TABLE I-continued

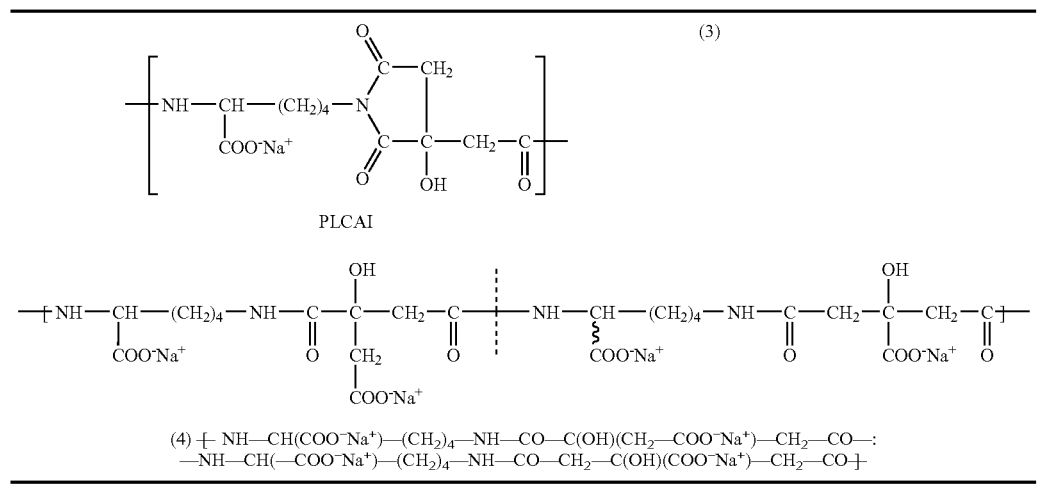

PLCAI (4) ⁺[— NH—CH(COO⁻Na⁺)—(CH₂)₄—NH—CO—C(OH)(CH₂—COO⁻Na⁺)—CH₂—CO—:
—NH—CH(—COO⁻Na⁺)—(CH₂)₄—NH—CO—CH₂—C(OH)(COO⁻Na⁺)—CH₂—CO—]⁺

As regards the method for preparing release systems according to the invention, as a general rule, the complexes are formed by mixing a solution of the polyelectrolyte with the active principle compound to be protected and progressively released. Preferably, the complexing results in a powdery stoechiometric precipitate, which may be ground and subsequently screened to facilitate incorporation in the matrix.

The complex may be freeze-dried, so as to obtain a dry form; oven drying of same may also be envisaged.

The incorporation of the complex in the matrix, leading to the ternary matrix-complexing agent-active principle system, is carried out by any means compatible with the type of complexes and matrixes. It is possible to use a matrix in flexible form and, to fold the film, work at a temperature above Tg.

Typically, a matrix in film form, sometimes referred to as a "sheet" is used, whereon the powder complex is deposited, and the film is folded onto itself and the film is compressed a second time to obtain a new "sheet" wherein the active principle is dispersed. For this purpose, a standard press capable of operating at variable temperatures and producing films of some hundred microns in thickness may be used.

After the polyelectrolyte has been incorporated in the matrix, the degradation of the degradable complexing polyelectrolyte in the acid forming matrix is determined by the presence of water or physiological fluid.

The present invention encompasses combinations of complexes of compounds having opposite charges that are stable under physiological conditions and entrapment in a matrix forming acids capable of degrading the polyelectrolyte complexing agent of the active principle.

The stable complex cannot be dissociated through the law of mass action but only by varying the local pH (obtained by the degradation of the matrix) or by increasing the ionic force (which is not suitable for use inside a polymer matrix) so that the burst release is attenuated, or even eliminated, according to the invention.

Finally, according to the invention, releases of the compounds of interest are actually prolonged according to profiles, which are original, due to the complexing with the acid-sensitive polyelectrolyte, the concentration in the release phase varying over time over long periods (several dozen days dependent on the cases).

As regards the ratios by weight, the complex may be incorporated in a wide range of complex weight ratio values in the ternary system, ranging from 0.1 to 60% by weight of the total weight of the ternary system. It is preferable to use a more restricted range compatible with the pharmacokinetic results, such a preferred range is from 1 to 40% by weight of the complex with respect to the total weight of the ternary complex-polymer matrix system.

One of the advantages of the controlled release system is the stability thereof during the storage thereof. Indeed, since the degradation of the polymer, for example the degradable complexing polyanion in the acid forming matrix, is subject to the presence of water, the system remains stable during dry storage.

Alternatively, it may be envisaged to use the ternary matrix/polyelectrolyte complex-active principle system not in film form but in particle form. These particles may also be coated conventionally with PLAGA or PLA type polymers so as to provide additional modulation in the active principle release rate. The form of the matrix (microspheres, microparticles, sheets, implants, films, etc.) affects the degradation rate of said matrix and thus the release rate of the active principle. The form and dimensions of the controlled release system make it possible to adapt the degradation rate of the matrix and thus the formation of acid products degrading the polyelectrolyte partner.

BRIEF DESCRIPTION OF THE DRAWINGS

FIG. 2 represents the release profile of a PLCA/7P/PLA (37.5)GA(25) system (●); i.e., an active principle (7P) incorporated in a complex according to the invention (PLCA complexing agent) in a matrix (PLAGA), compared to the complex alone (PLCA/7P) (▲) or to the active principle alone, incorporated in the same matrix (7P/PLAGA) (■);

FIG. 3 represents the release profile of a PMLA/PLL/PLA (37.5)GA(25) system (●), i.e., an active principle (PLL) incorporated in a complex according to the invention (PMLA complexing agent) in a matrix (PLAGA), compared to the complex alone (PMLA/PLL) (▲) or to the active principle alone, incorporated in the same matrix PLL/PLAGA (■);

The invention will be understood more clearly in the light of appended figures and the examples below.

Figure 1:
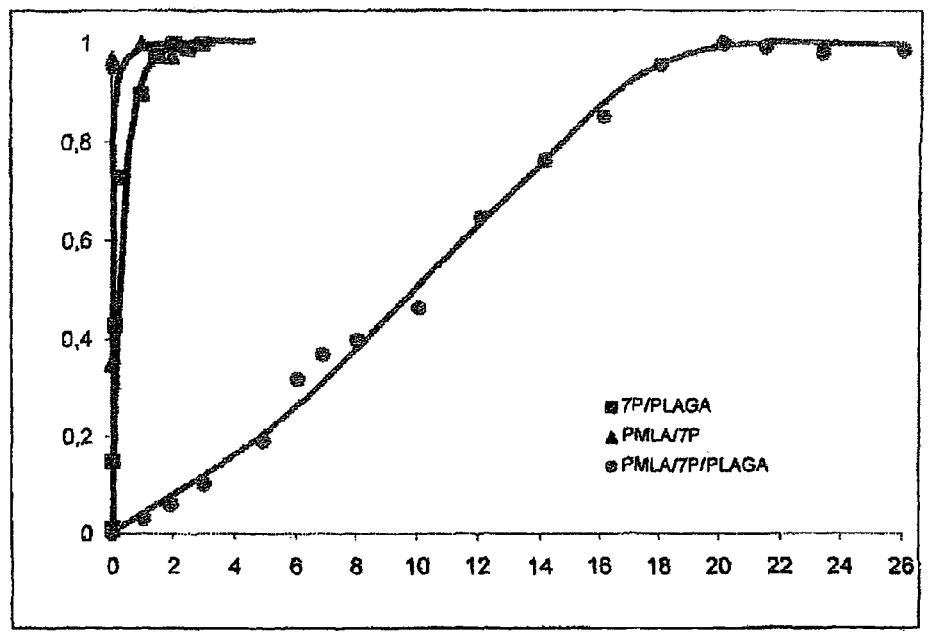
FIG. 1 represents the release profile of a PMLA/7P/PLA (37.5)GA(25) system (●), i.e., an active principle (7P) incorporated in a complex according to the invention (PMLA complexing agent) in a matrix (PLAGA), compared to the complex alone (PMLA/7P) (▲) or to the active principle alone, incorporated in the same matrix (7P/PLAGA) (■)

FIG. 1 represents the release profile of an active principle (7P) incorporated in a complex according to the invention (PMLA complexing agent) in a matrix (PLAGA) (●), compared to the complex alone (▲) or to the active principle alone (■), incorporated in the same matrix. In FIG. 1, the degradation in days is recorded on the X-axis, and the release rate is recorded on the Y-axis. FIGS. 2 and 3 relate to similar examples with a further complexing agent (PLCA) and a polyelectrolytic active principle template (PLL), respectively.

The applicant demonstrated, as can be seen in the examples, that similar results may be obtained with different active principles for the same matrix-complexing agent pair in line with control by means of the matrix degradation and thus by the acid residue appearance kinetics.

Figure 4:
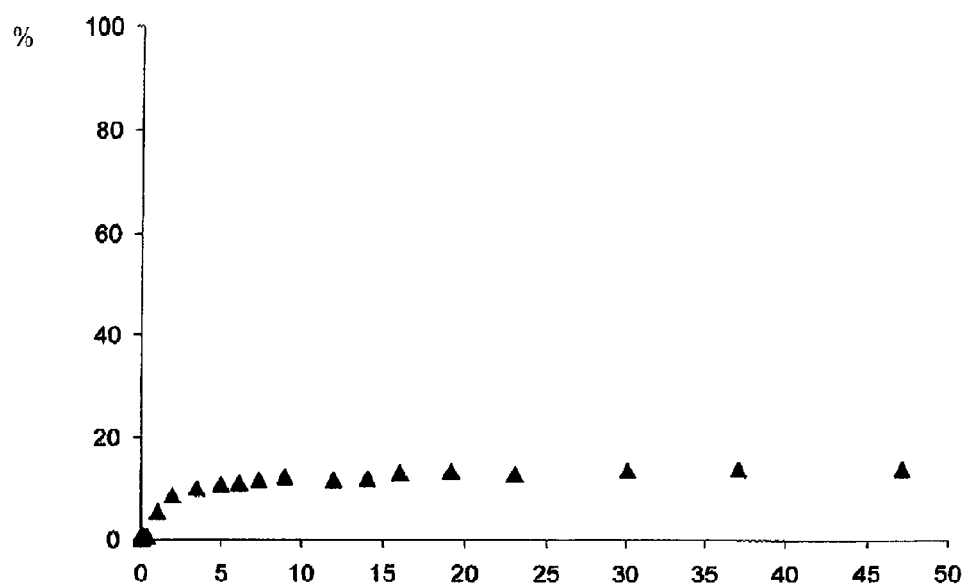
FIG. 4 illustrates a release profile (release percentage on Y-axis, as a function of time on X-axis, in days: 0 to 50 days) when the acid-sensitive complexing agent is incorporated in a stable matrix (PCL)
Figure 5:
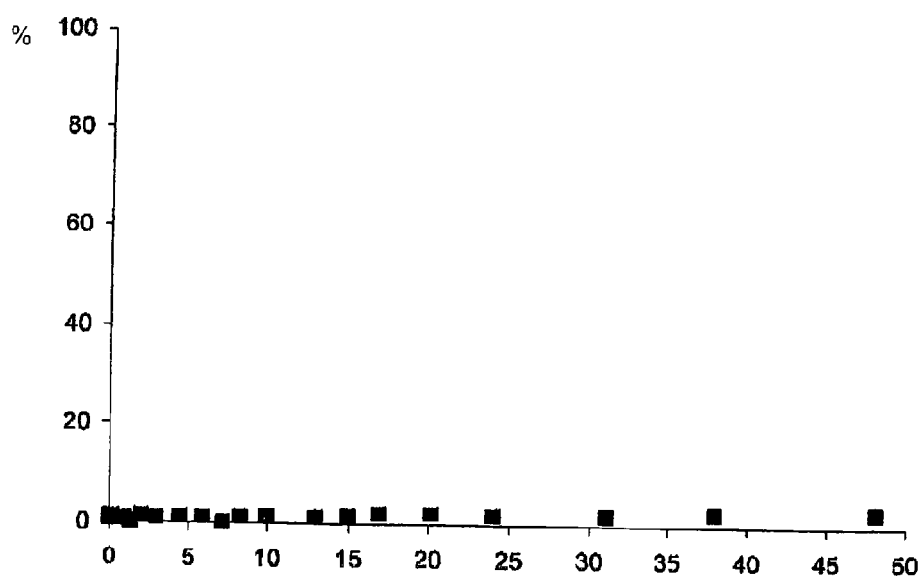
FIG. 5 illustrates a release profile (release percentage on Y-axis, as a function of time on X-axis, in days: 0 to 50 days) when a non-acid-sensitive complexing agent is incorporated in a degradable matrix: PMA-PLL complex incorporated in the matrix PLA(37.5)GA(25).

For comparative purposes, FIGS. 4 and 5 illustrate release profiles (release percentage on Y-axis, as a function of time on X-axis, in days: 0 to 50 days) when the acid-sensitive complexing agent is incorporated in a stable matrix and when a non-acid-sensitive complexing agent is incorporated in a degradable matrix.

The results obtained in the comparative examples for a stable matrix associated with an acid-sensitive complexing agent and that of a degradable matrix associated with an acid-sensitive complexing agent respectively demonstrate the importance of the choice of a hydrolytically degradable matrix forming acid degradation products, and the importance of the choice of an acid-sensitive complexing agent which is degraded under the effect of the degradation of the matrix to enable the prolonged release of the active principle.

Examples 1 to 5

Preparation of Systems for the Controlled Release of Arg-Lys-Arg-Ser-Arg-Lys-Glu (7P) and Polylysine (PLL)

1) Reagents Used:
Complexing Agent:
PMLA,Na (Mw=30,000 g/mol)
PLCA,Na (Mw=40,000 g/mol, Mn=20,000 g/mol)
Matrix:
PLA(37.5)GA(25) (Mw=30,000 g/mol, Mn=9000 g/mol) for examples 1 to 4
PLA50 (Mw=50,000 g/mol) for example 5
Active Principle or Polyelectrolyte Template:
The above heptapeptide (7P), a protein kinase inhibitor, has a molecular weight of 959 g/mol and contains 5 overall positive charges.
Polylysine (PLL) has a molecular weight Mw of 12,000 g/mol and contains one positive charge per structural unit.
7P and PLL are particularly available from the suppliers Sigma-Aldrich, Bachem and American Peptide Company.

2) Preparation of Four Complexes
Ex.1:
Typically, 500 μl of aqueous solution containing 25 mg of PLL,HBr was added to 1 ml of aqueous solution containing 16.7 mg of PMLA,Na. 26 mg of PMLA-PLL solid complex (yield=88%) was retrieved after centrifuging the mixture and drying the precipitate.
Ex. 2:
In the same way, 28 mg of PLCA-PLL (yield=84%) was obtained from 20.7 mg of PLCA,Na and 25 mg of PLL,Hbr.
Ex. 3:
Similarly, 22.3 mg of PLCA-7P solid complex (yield=63%) was obtained from 19.1 mg of PLCA,Na and 25 mg of 7P.
Ex. 4:
Similarly, 23.7 mg of PMLA-7P solid complex (yield=75%) was obtained from 15.3 mg of PMLA,Na and 25 mg of 7P.

The solid complexes were then ground with a mortar and a powder was obtained.

3) Incorporation of Complexes in the Matrix
Typically, for the systems in examples 1 to 4, 1 g of PLA (37.5)GA(25) was compressed in a press (CARVER 4120 CE) at 50° C. and a film of some hundred microns in thickness was obtained.

The complex powder was deposited about the centre of the film, which was folded before compressing the film a second time under the same conditions. The folding and compression steps are repeated three times. The entire complex was thus distributed homogeneously in the matrix.

For the comparative example in which the active principle is incorporated alone in the matrix, incorporation is carried out under the same conditions as those of the complex.

Incorporation is carried out at an incorporation rate by weight of the complex in the matrix of 4% by weight, with a final matrix thickness of 0.5 mm, for the systems in examples 1 to 4.

Furthermore, with the same method, when 1 g of PLA50 replaced 1 g of PLAGA, compression takes place at 100° C. and a film of some hundred microns in thickness was obtained (example 5).

Examples 6 to 8

Release of Ionic Active Principle

For each of the complexes in examples 1 to 4, the following three systems were studied: the binary solid polyelectrolyte/active principle complex system (▲ on the curves), the binary matrix/active principle system (■ on the curves), and the ternary matrix/solid polyelectrolyte-active principle complex system (● on the curves).

Each of the three systems was introduced into pill boxes containing 5 ml of PBS (template physiological conditions) and placed under stirring at 37° C.

Regularly, 20 μl of solution is sampled for analysis and replaced by the same volume of PBS. The 20 μl of sampled solution is added to a solution containing 1.2 ml of borate buffer (0.1 m concentration, pH=9.3). 20 μl of TNBS (trinitrobenzenesulphonic acid, concentration 0.03 M) is then added to the mixture left to stand for 2 hours. The quantity of amine groups (and thus active ingredient) released is measured by means of UV-Visible spectroscopy at 420 nm by means of calibration curves.

Release Profiles—Results
The degradation of the matrix supplies acid products which catalyse the degradation of the polyelectrolyte-active principle complex by degrading the polyelectrolyte partner selectively. The degradation rate of the matrix directly determines the release rate of the bioactive ionic substance.

In FIG. 1, for the 7P/PLAGA (■) and PMLA/7P (▲) systems, the peptide 7P is released in less than 2 days, or even in a few hours for the binary PMLA/7P system (▲).

It emerged that the ternary PMLA/7P/PLA(37.5)GA(25) system (●) in FIG. 1, similar to the systems PMLA/PLL/PLA (37.5)GA(25) (●) in FIG. 3, PLCA/PLL/PLA(37.5)GA(25) (●) in FIG. 2 and PLCA/PLL/PLA(37.5)GA(25) (not shown) enable a gain in prolonged PLL and 7P release over 18 days compared to the binary matrix/active principle or polyelectrolyte-active principle systems.

Furthermore, it appears that the binary PLCA-PLL system does not enable the release of PLL under the template physiological conditions used: however, the ternary system has the advantage of rendering PLL bioavailable.

Using PLA50 instead of PLAGA as a degradable matrix for PLL incorporate according to example 5, the release of the active principle is delayed considerably and is performed after three months.

Example 9

The ternary PLA50/PMLA/7P system prepared under the same conditions as those in example 5 was also studied. A release after 3 months is also demonstrated.

Examples 10 to 12

Similar release profiles were obtained with systems similar to those in examples 1, 3 and 4, the ratio by weight being increased from 4% to a ratio of 8% in the matrix. The matrix eventually obtained has a thickness of 1.3 mm.

Examples 13-14

Stable precipitate complexes were prepared in a similar manner to that in examples 1 and 2, with leuprolide in the PLL phase complexed with PMLA and with PLCA.

Examples 15-16

PMLA-Bursin and PLCA-Bursin complexes was also prepared, not precipitated as in examples 1 to 4 but freeze-dried, the freeze-dried products being incorporated in a sheet of PLAGA.

Examples 17

Comparison

With the PLCA,Na complexing agent and the PLL active principle (polyelectrolyte template), the PLCA-PLL complex was prepared and was incorporated into the poly(ε-caprolactone) matrix (PCL), as above in example 2. The incorporation was carried out at an incorporation ratio by weight of the complex in the matrix of 4% by weight, with a final matrix thickness of 0.5 mm after compression at 70° C.

As can be seen in FIG. 4, a slight burst attributable to the surface washing appears. It corresponds to 10% of the total quantity of PLL. Even after 50 days, less than 15% of the total PLL is released.

Example 18

Comparison with the non-acid-sensitive complexing agent poly(methacrylic acid) (PMA,Na) and the active principle (polyelectrolyte template) PLL, the PMA-PLL complex was prepared by adding 500 μl of aqueous solution containing 25 mg of PLL, HBr to 1 ml of aqueous solution containing 12.9 mg of PMA, Na. 18 mg of solid PMA-PLL complex (yield=71%) was retrieved, after centrifuging the mixture and drying the precipitate. The PMA-PLL complex was incorporated in the matrix PLA(37.5)GA(25), as above in examples 1 to 4. Incorporation was carried out at an incorporation ratio by weight of the complex in the matrix of 5% by weight, with a final matrix thickness of 0.15 mm after compression at 60° C.

As can be seen in FIG. 5, even after 50 days, less than 3% of the total PLL is released.

Example 19

With poly(α-aminoserinate) (PSA) and the active principle (polyelectrolyte template) polyacrylic acid (PAA, Na), the PPA-PSa complex was prepared by adding 500 it of aqueous solution containing 10.5 mg of PSA,Hbr to 1 ml of aqueous solution containing 5.5 mg of PPA,Na. 6.8 mg of solid PAA-PSA complex (yield=68%) was retrieved after centrifuging the mixture and drying the precipitate. The PAA-PSA complex was incorporated in the same way as in examples 1 to 4 in a PLA (37.5)GA(25) matrix. Incorporation was carried out at an incorporation ratio by weight of the complex in the matrix of 4.5% by weight, with a final matrix thickness of 0.22 mm after compression at 60° C.

After three weeks, it was observed that the release profile of PAA (degradable matrix+acid-sensitive polyanionic complexing agent) is equivalent to that of an acid-sensitive polyanionic complexing agent and an active principle or polycationic type polyelectrolyte template in examples 6 to 8.

REFERENCES

[1] *Release of the polyanion from polyelectrolyte complexes by selective degradation of the polycation* T. Etrych, M. Boustta, L. Leclercq et M. Vert—J. Bioact. Comp. Polym., Vol. 21, pp. 89-105 (2006).

[2] *Degradable polymers as tools for polyelectrolyte complex analysis*, L. Leclercq, M. Boustta et M. Vert—ACS Symposium Series 939 *"Degradable polymers and materials"*—Editeurs K. C. Khemani and C. Scholz, Chapter 17, pp. 267-281 (2006).

[3] *Influence of the poly(lactide-co-glycolide) type on the leuprolide release from in situ forming microparticle systems* X. Luan et R. Bodmeier—J. Controlled Rel., Vol. 110, pp. 266-272 (2006).

[4] *Synthetic poly(β-hydroxyalkanoates) with carboxylic acid or primary amine pendent groups and their, complexes*, Rossignol, H., Boustta, M. & Vert, M., International Journal of Biological Macromolecules 25, 255-264 (1999).

[5] *Synthesis, properties and in vitro degradation of carboxyl-bearing PCL*, Gimenez, S., Ponsart, S., Coudane, J. & Vert, M., Journal of Bioactive and Compatible Polymers 16, 32-46 (2001).

[6] *Hydrolytic Degradation of benzylated poly(beta-malic acid)*, Mauduit, J.; Boustta, M. et Vert, M., Journal Biomaterials Science, Polymer Edition 7, 207-220 (1995).

[7] *Polylactic and polyglycolic acids as drug delivery carrier* L. Brannon-Pepas & M. Vert (2000) Handbook of Pharmaceutical Controlled Release Technology, Editeurs: D. L. Wise, A. Kilbanov, R. Langer, A. Mikos, L. Brannon-Pepas, N. A. Peppas, D. J. Trantalo, G. E. Wnek & M. J. Yaszemski, Marcel Dekker, New-York, pp 99-130.

[8] *Biopolymers and artificial biopolymers in biomedical applications, an overview.* Vert, M., in Biorelated Polymers: Sustainable Polymer Science and Technology. Editeurs: Chiellini et al., Kluwer Academic/Plenum Publishers, (2001).

The invention claimed is:

1. A system for the controlled release of an active principle, the system consisting of:
 (a) a degradable polymer matrix able to form acid compounds when the polymer matrix is hydrolytically degraded, and
 (b) a polyelectrolytic complex of the active principle with a polyelectrolytic polymer partner of opposite net charge, wherein
 said active principle has at least one electrostatic charge and said polyelectrolytic partner has an opposite charge, said complex being stoichiometric in terms of opposite electric charges,
 said polyelectrolytic polymer partner is acid-sensitive and suitable of being degraded by said acid compounds formed when the polymer matrix is hydrolytically degraded, and
 said complex is incorporated within the degradable polymer matrix.

2. The system according to claim 1, wherein the polymer matrix comprises poly(α-hydroxy acid), polyanhydride or polycaprolactone.

3. The system according to claim 1, wherein the polymer matrix comprises poly(lactide-co-glycolide).

4. The system according to claim 1, wherein said polyelectrolytic polymer partner comprises poly(malic acid), poly(lysine citramide) or poly(amino serinate).

5. The system according to claim 1, wherein the polyelectrolytic complex is formed by ionic pairing between a basic active principle and a polyanion complexing agent selected from poly(malic acid) and poly(lysine citramide).

6. The system according to claim 1, wherein the active principle comprises multiple amines.

7. The system according to claim 1, wherein the polyelectrolytic complex is formed by ionic pairing between an acidic active principle and an acid-sensitive poly(amino serinate).

8. The system according to claim 1, wherein the polyelectrolytic complex is insoluble in aqueous medium.

9. The system according to claim 1, wherein the active principle is a polyelectrolyte.

10. The system according to claim 1, wherein the polyelectrolytic complex is present in said system in a range of from 0.1% to 60% by weight.

11. A method for preparing the controlled release system of claim 1,
 said method comprising:
 forming a polyelectrolytic complex between said active principle having at least one electrostatic charge and said acid-sensitive polyelectrolytic polymer partner of opposite charge, said complex being stable under the pH, salinity and temperature conditions of physiological media; and
 incorporating said complex within the degradable polymer matrix.

12. A method of controlling the release of an active principle, comprising providing the system according to claim 1, and utilizing said system to control the release of said active principle.

13. The method of claim 12, wherein said polymer matrix comprises poly(α-hydroxy acid), polyanhydride or polycaprolactone.

14. The method of claim 12, wherein said polymer matrix comprises poly(lactic acid-co-glycolic acid) or poly(lactic acid).

15. The method of claim 12, wherein the polyelectrolytic polymer partner is selected from the group consisting of poly(malic acid), poly(lysine citramide) and poly(amino serinate).

* * * * *

UNITED STATES PATENT AND TRADEMARK OFFICE
CERTIFICATE OF CORRECTION

PATENT NO. : 8,709,481 B2  
APPLICATION NO. : 12/669252  
DATED : April 29, 2014  
INVENTOR(S) : Vert et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 610 days.

Signed and Sealed this

Twenty-ninth Day of September, 2015

Michelle K. Lee  
*Director of the United States Patent and Trademark Office*